(12) United States Patent
Iwaya et al.

(10) Patent No.: US 7,102,031 B2
(45) Date of Patent: Sep. 5, 2006

(54) METHOD FOR PRODUCING DIENE COMPOUND

(75) Inventors: Masao Iwaya, Yokohama (JP);
Hidekazu Okamoto, Yokohama (JP);
Kazuya Oharu, Yokohama (JP)

(73) Assignee: Asahi Glass Company, Limited, Tokyo (JP)

(*) Notice: Subject to any disclaimer, the term of this patent is extended or adjusted under 35 U.S.C. 154(b) by 86 days.

(21) Appl. No.: 10/864,497

(22) Filed: Jun. 10, 2004

(65) Prior Publication Data

US 2005/0038300 A1    Feb. 17, 2005

Related U.S. Application Data

(63) Continuation of application No. PCT/JP02/13019, filed on Dec. 12, 2002.

(30) Foreign Application Priority Data

Dec. 12, 2001 (JP) ............... 2001-378924

(51) Int. Cl.
*C07C 41/18* (2006.01)
(52) U.S. Cl. ............ 562/682; 568/683; 568/684; 568/685
(58) Field of Classification Search ............ 568/682, 568/683, 684, 685; 525/909, 925; 528/401, 528/425; 562/849, 851, 852; 570/153, 160; 549/472, 504
See application file for complete search history.

(56) References Cited

FOREIGN PATENT DOCUMENTS

| EP | 0 303 292 A2 | 2/1989 |
|---|---|---|
| EP | 1 160 231 A1 | 12/2001 |
| JP | 1-143843 A | 6/1989 |
| JP | 2-42038 A | 2/1990 |
| JP | 2-311438 A | 12/1990 |
| JP | 4-346956 | * 12/1992 |
| JP | 4-346956 A | 12/1992 |

OTHER PUBLICATIONS

Kazuya et al., Fluorinated Compound and its Production, Dec. 12, 1992, Patent Abstracts of Japan.*

Suzanne T. Purrington, et al., "[3,3]-Sigmatropic rearrangements of fluorinated compounds" Journal of Fluorine Chemistry, vol. 56, No. 2, XP-002370018, 1992, pp. 165-173.

* cited by examiner

*Primary Examiner*—Rosalynd Keys
(74) *Attorney, Agent, or Firm*—Oblon, Spivak, McClelland, Maier & Neustadt, P.C.

(57) ABSTRACT

It is an object to obtain from a mixture of a specific diene compound (1) and a compound (2) with the same molecular weight and molecular formula hard to separate by distillation, the diene compound (1) in high purity without using any special reagent or complicated technique.

Namely, the present invention provides a method of inducing the Claisen rearrangement reaction of the compound (2) in a mixture containing $CR^1R^2=CR^3CFR^4CR^5R^6OCR^7=CR^8R^9$ (1) and $CFR^1R^2CR^3=CR^4CR^5R^6OCR^7=CR^8R^9$ (2), and separating the diene compound (1) from a Claisen rearrangement reaction product; or converting the Claisen rearrangement reaction product into a derivative and then separating the diene compound (1) from the derivative of the Claisen rearrangement reaction product. Wherein, $R^1$ to $R^9$ each represent a fluorine atom or the like.

12 Claims, No Drawings

METHOD FOR PRODUCING DIENE COMPOUND

TECHNICAL FIELD

The present invention relates to a method for producing a diene compound in high purity. Furthermore, the present invention relates to a method for producing a diene compound with use of the Claisen rearrangement reaction.

BACKGROUND ART

In production of an olefin compound, a rearrangement reaction of a double bond can occur during a production process or after production to yield a structural isomer which has the same molecular formula but an unsaturated bond at a different position. If the structural isomer has the reactivity comparable to that of the intended olefin compound, there will arise such a problem that it changes the properties of the olefin compound. On the other hand, if the reactivity of the structural isomer is low, there will arise another problem that it interferes with the reaction of the intended olefin.

There is still another problem that the structural isomer has a boiling point too close to that of the intended olefin to separate it by distillation. Furthermore, there was still another problem that even if an attempt to separate them was made by means of azeotropic distillation, extractive distillation or chromatography available for separation of compounds having boiling points close to each other, the properties of the structural isomer (e.g., polarity and the like) were so similar to those of the intended olefin that it was difficult to separate them from each other.

Under these circumstances, the following methods have been proposed to produce only the intended olefin, while producing a structural isomer as little as possible.

(a) A method wherein a compound represented by the following formula (A1-2) is obtained by vapor-phase pyrolysis of a compound represented by the following formula (A1-1), and then a dechlorination reaction is conducted in the presence of zinc to form a 3-butenyl group, thereby obtaining 3-butenyl vinyl ether represented by the following formula (A) (JP-A-1-143843).

FC(O)CF(CF₃)OCF₂CF₂CFClCF₂Cl  (A1-1)

CF₂=CFOCF₂CF₂CFClCF₂Cl  (A1-2)

CF₂=CFOCF₂CF₂CF=CF₂  (A)

(b) A method wherein a compound represented by the following formula (A2-2a) is produced by pyrolysis of a compound represented by the following formula (A2-1) as a starting material, and then a dechlorination reaction of the compound is conducted, thereby obtaining 3-butenyl vinyl ether represented by the following formula (A) (JP-A-2-311438).

CF₂ClCFClOCF₂CF₂CF₂CF₂COF  (A2-1)

CF₂ClCFClOCF₂CF₂CF=CF₂  (A2-2a)

CF₂=CFOCF₂CF₂CF=CF₂  (A)

CF₂ClCFClOCF₂CF=CFCF₃  (A2-2b)

CF₂=CFOCF₂CF=CFCF₃  (A-3)

However, multiple steps were required for synthesis of the compound represented by the formula (A1-1) used in the method (a). Furthermore, there was a problem that the production of the compound needed to use reagents difficult to handle, such as fuming sulfuric acid, iodine monochloride, and so on.

Furthermore, the method (b) was proved to have a problem that a rearrangement reaction of a double bond took place in a 3-butenyl group having a fluorine atom at the 1-position, in the compound represented by the formula (A2-2a), thereby producing a thermodynamically stabler compound represented by the formula (A2-2b). If the dechlorination is conducted in the presence of the compound of the formula (A2-2b), there will arise a problem that a compound represented by the formula (A-3) is mixed into the final product.

Here, the compound represented by the formula (A2-2a) has much the same properties, including the boiling point and others, as the compound represented by the formula (A2-2b), and the compound represented by the formula (A) also has much the same properties, including the boiling point and others, as the compound represented by the formula (A-3). Therefore, there was a problem that it was difficult to separate these compounds and it was infeasible to obtain the compound represented by the formula (A) in high purity.

The compound represented by the formula (A), produced by these methods, is useful as a raw-monomer for a fluorocarbon resin. However, in a case where the compound represented by the formula (A) was polymerized in the presence of the compound represented by the formula (A-3), there was a problem that the polymerization was significantly hindered, so as to result in failure in production of a fluorocarbon polymer having a high molecular weight.

On the other hand, the Claisen rearrangement reaction itself is a known reaction. As examples of the Claisen rearrangement reaction in a fluorine-containing compound, there have been reported examples in compounds such as CF₂=CFOCH₂CH=CH₂, CF₃ (CF₃) C=CFOCH₂CH=CH₂, Cl₂C=CFOCH₂CH=CH₂, ClFC=CFOCH₂CH=CH₂ and H(CF₃)C=CH(CF₃)=CH₂CH=CH₂ (J. Fluorine Chemistry, 1992, 56, 165), examples of CH₂=CH(CF₃)OCH₂CH=CH₂ and CH₂=CHOCH(CF₃)CH=CH₂ (J. Org. Chem., 1990, 55, 1813), an example of the Claisen rearrangement reaction from CF₂=CFCF₂OCF=CF₂ to CF₂=CFCF₂CF₂CF=O (JP-A-2-42038), and so on.

However, none of these documents reported about the Claisen rearrangement in a compound having a 2-butenyl skeleton with a fluorine atom bonded at the 4-position. A document describing such an example is one wherein CH₂=CHOCH₂CH=CHCF₂PO(OCH₂CH₃)₂ with a group containing a phosphorus atom at the 4-position is converted to CH₂=CHCH(CF₂PO(OCH₂CH₃)₂)CH₂CH=O by heating at 140° C. (Chem. Commun., 2000, 1691). However, the reaction was conducted under the same conditions with the compound represented by the formula (2) of the present invention, which contained no phosphorus atom, and found that the Claisen rearrangement reaction did not proceed at all.

SUMMARY OF THE INVENTION

An object of the present invention is obtaining a diene compound represented by formula (1) in higher purity, by making use of the Claisen rearrangement reaction of a compound represented by formula (2) to remove it from a mixture of the diene compound represented by the formula (1) having a possibility of occurrence of a rearrangement reaction of a double bond and the compound represented by the formula (2) having a structure resulting from rearrangement of the double bond of the diene compound represented by the formula (1). Furthermore, the present invention provides a method for producing a diene compound by inducing the Claisen rearrangement reaction in a novel substrate which has not ever been applied.

DISCLOSURE OF THE INVENTION

Namely, the present invention relates to each invention below.

1. A method for producing a diene compound represented by the following formula (1) in high purity, which comprises inducing the Claisen rearrangement reaction of a compound represented by the following formula (2), in a mixture comprising the diene compound represented by the formula (1) and the compound represented by the formula (2), to produce a product comprising a Claisen rearrangement reaction product and the diene compound represented by the formula (1), and separating the diene compound represented by the formula (1) from the Claisen rearrangement reaction product, or converting the Claisen rearrangement reaction product into a derivative thereof and then separating the diene compound represented by the formula (1) from the derivative of the Claisen rearrangement reaction product, wherein $R^1$ to $R^9$ in the following formulae, which may be the same or different from each other, represent a hydrogen atom, a halogen atom, a monovalent hydrocarbon group, an etheric oxygen atom-containing monovalent hydrocarbon group, a halogenated monovalent hydrocarbon group or a halogenated etheric oxygen atom-containing monovalent hydrocarbon group.

$CR^1R^2=CR^3CFR^4CR^5R^6OCR^7=CR^8R^9$ (1)

$CFR^1R^2CR^3=CR^4CR^5R^6OCR^7=CR^8R^9$ (2)

2. The method according to the above 1, wherein a compound represented by the following formula (3) is produced by the Claisen rearrangement reaction, wherein symbols in the following formula have the same meanings as those defined above.

$CR^5R^6=CR^4CR^3(CFR^1R^2)CR^8R^9CR^7=O$ (3)

3. The method according to the above 1 or 2, wherein a compound represented by the following formula (3a) is produced by the Claisen rearrangement reaction where the compound represented by the formula (2) is a compound represented by the following formula (2a), wherein symbols in the following formulae have the same meanings as those defined above.

$CFR^1R^2CF=CR^4CR^5R^6OCF=CR^8R^9$ (2a)

$CR^5R^6=CR^4C(CFR^1R^2)=CR^8R^9$ (3a)

4. The method according to any one of the above 1, 2 and 3, wherein $R^1$ to $R^9$, which may be the same or different from each other, represent a fluorine atom, a hydrogen atom, a chlorine atom, a trifluoromethyl group or a trifluoromethoxy group.

5. The method according to any one of the above 1, 2, 3 and 4, wherein all of $R^1$ to $R^9$ independently represent a fluorine atom.

6. The method according to any one of the above 1, 2, 3, 4 and 5, wherein the Claisen rearrangement reaction is induced by heating the mixture in a vapor phase.

7. The method according to the above 6, wherein the Claisen rearrangement reaction is induced in the presence of an inert gas, or an inert solvent which turns into a gas at a reaction temperature.

8. The method according to any one of the above 1 to 7, wherein the Claisen rearrangement reaction is conducted in the presence of a polymerization inhibitor.

9. The method according to any one of the above 1 to 8, wherein the Claisen rearrangement reaction is induced by heating the mixture at a temperature of from 150 to 400° C.

10. The method according to any one of the above 1 to 9, wherein the compound represented by the formula (2) is a compound produced by a rearrangement reaction of a double bond in the compound represented by the formula (1), or a compound produced by a dechlorination reaction of a compound represented by the following formula (1B-3), wherein symbols in the following formula have the same meanings as those defined above.

$CFR^1R^2CR^3=CR^4CR^5R^6OCClR^7—CClR^8R^9$ (1B-3)

11. A method for producing a fluorine-containing polymer, which comprises polymerizing the diene compound of the formula (1) in high purity obtained by any one of the methods defined in the above 1 to 10, or polymerizing the diene compound and a compound polymerizable with the diene compound.

12. A method for producing a compound represented by the following formula (3), which comprises carrying out the Claisen rearrangement reaction in a compound represented by the following formula (2), wherein $R^1$ to $R^9$ in the following formulae, which may be the same or different from each other, represent a hydrogen atom, a halogen atom, a monovalent hydrocarbon group, an etheric oxygen atom-containing monovalent hydrocarbon group, a halogenated monovalent hydrocarbon group or a halogenated etheric oxygen atom-containing monovalent hydrocarbon group.

$CFR^1R^2CR^3=CR^4CR^5R^6OCR^7=CR^8R^9$ (2)

$CR^5R^6=CR^4CR^3(CFR^1R^2)CR^8R^9CR^7=O$ (3)

13. A method for producing a compound represented by the following formula (3a), which comprises heating the compound represented by the following formula (2a) in the presence of soda ash or glass beads, wherein $R^1$, $R^2$, $R^4$, $R^5$, $R^6$, $R^8$ and $R^9$ in the following formulae, which may be the same or different from each other, represent a hydrogen atom, a halogen atom, a monovalent hydrocarbon group, an etheric oxygen atom-containing monovalent hydrocarbon group, a halogenated monovalent hydrocarbon group or a halogenated etheric oxygen atom-containing monovalent hydrocarbon group.

$CFR^1R^2CF=CR^4CR^5R^6OCF=CR^8R^9$ (2a)

$CR^5R^6=CR^4C(CFRR^2)=CRR^9$ (3a)

BEST MODE FOR CARRYING OUT THE INVENTION

In the present specification, the diene compound represented by the formula (1), will be referred to as the diene compound (1). The other compounds will also be referred to in the same manner.

In the diene compound (1), $R^1$ to $R^9$, which may be the same or different from each other, represent a hydrogen atom, a halogen atom, a monovalent hydrocarbon group, an etheric oxygen atom-containing monovalent hydrocarbon group, a halogenated monovalent hydrocarbon group or a halogenated etheric oxygen atom-containing monovalent hydrocarbon group. The halogen atom is preferably a fluorine atom or a chlorine atom, particularly preferably a fluorine atom. The monovalent hydrocarbon group is preferably an alkyl group. The etheric oxygen atom-containing monovalent hydrocarbon group is preferably an alkoxy group.

In a case where $R^1$ to $R^9$ independently are a halogenated group, the halogenated group is preferably a fluorinated group. The halogenated monovalent hydrocarbon group is preferably a fluoroalkyl group, particularly preferably a perfluoroalkyl group. The halogenated etheric oxygen atom-containing monovalent hydrocarbon group is preferably a fluoroalkoxy group, specifically preferably a perfluoroalkoxy group.

$R^1$ to $R^9$ independently are preferably a hydrogen atom, a fluorine atom, a fluorinated monovalent hydrocarbon group or a fluorinated etheric oxygen atom-containing monovalent hydrocarbon group, particularly preferably a fluorine atom or a fluorinated monovalent saturated organic group, and, especially preferably a fluorine atom, a hydrogen atom, a fluoroalkyl group or a fluoroalkoxy group. Furthermore, $R^1$ to $R^9$ independently are preferably a fluorine atom or a perfluorinated one of these groups, particularly preferably a fluorine atom, a trifluoromethyl group or a trifluoromethoxy group.

The diene compound (1) of the present invention is preferably a compound wherein $R^1$, $R^2$, $R^7$ and $R^8$ independently are a fluorine atom, because a compound having a polymerizable unsaturated bond is particularly useful. Furthermore, the rest groups ($R^3$ to $R^6$ and $R^9$) independently are preferably a fluorine atom, a perfluoroalkyl group or a perfluoroalkoxy group, particularly preferably a fluorine atom.

There are no particular restrictions on how to obtain the diene compound (1). Specific examples of the diene compound (1) include the compounds listed below. Configurations of the two double bonds in the compounds may be each either E or Z.

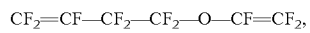
$CF_2=CF—CF_2—CF_2—O—CF=CF_2,$

$CF_2=CF—CF_2—CF(CF_3)—O—CF=CF_2,$

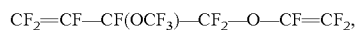
$CF_2=CF—CF(OCF_3)—CF_2—O—CF=CF_2,$

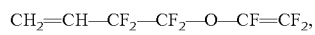
$CH_2=CH—CF_2—CF_2—O—CF=CF_2,$

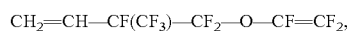
$CH_2=CH—CF(CF_3)—CF_2—O—CF=CF_2,$

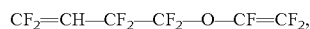
$CF_2=CH—CF_2—CF_2—O—CF=CF_2,$

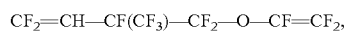
$CF_2=CH—CF(CF_3)—CF_2—O—CF=CF_2,$

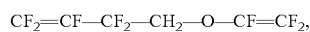
$CF_2=CF—CF_2—CH_2—O—CF=CF_2,$

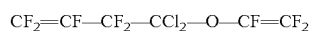
$CF_2=CF—CF_2—CCl_2—O—CF=CF_2$ and

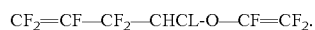
$CF_2=CF—CF_2—CHCL—O—CF=CF_2.$

The present invention uses the mixture comprising the diene compound (1) and the compound (2). The groups ($R^1$ to $R^9$) in the compound (2) have the same meanings as those defined above, and correspond to those in the diene compound (1). These compounds are those having a 2-butenyl- skeleton in which a fluorine atom is bonded at the 4-position. Configurations of the two double bonds in the compound (2) may be each either E or Z.

$CF_3—CF=CF—CF_2—O—CF=CF_2,$

$CF_3—CF=CF—CF(CF_3)—O—CF=CF_2,$

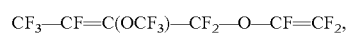
$CF_3—CF=C(OCF_3)—CF_2—O—CF=CF_2,$

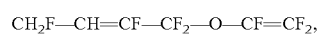
$CH_2F—CH=CF—CF_2—O—CF=CF_2,$

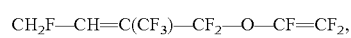
$CH_2F—CH=C(CF_3)—CF_2—O—CF=CF_2,$

$CHF_2—CH=CF—CF_2—O—CF=CF_2,$

$CF_3—CH=C(CF_3)—CF_2—O—CF=CF_2,$

$CF_3—CF=CF—CH_2—O—CF=CF_2,$

$CF_3—CF=CF—CCl_2—O—CF=CF_2$ and

$CF_3—CF=CF—CHCl—O—CF=CF_2.$

The upper limit of the proportion of the compound (2) in the mixture is preferably 50% by mass, particularly preferably 10% by mass as a proportion of the compound (2) to the total amount of the diene compound (1) and the compound (2). On the other hand, the lower limit of the proportion of the compound (2) is not particularly restricted, and in an ordinary case, it is preferably 0.003% by mass, particularly preferably 0.03% by mass as a proportion of the compound (2) to the total amount of the diene compound (1) and the compound (2). By the method of the present invention, the compound (2) can be separated even though the amount of the compound (2) is about 300 ppm by mass; therefore, the diene compound (1) can be produced in high purity.

There are no particular restrictions on how to obtain the compound (2), but the compound (2) in the present invention is preferably a compound produced by occurrence of the rearrangement reaction of the double bond in the diene compound (1). Since the diene compound (1) is a compound having a characteristic structure in which a fluorine atom is bonded to the carbon atom having $R^4$ bonded, it is a compound subject to the rearrangement reaction of the double bond. Occurrence of the rearrangement reaction will result in producing the compound (2).

For example, the rearrangement reaction of the following compound (1a-1) wherein all of $R^1$ to $R^9$ in the diene compound (1) are a fluorine atom, proceeds in the mechanism described below, and the resulting product is normally a mixture of the compound (1a-1) and the compound (2a-1).

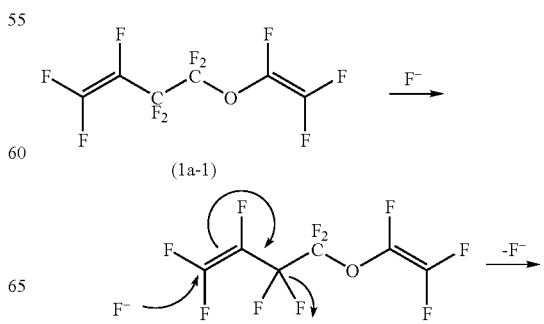

-continued

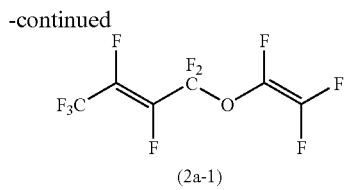

(2a-1)

The mixture in the present invention is preferably a mixture of the diene compound (1) and the compound (2), containing the compound (2) produced by the rearrangement reaction of the double bond in the diene compound (1). Namely, the present invention is preferably applied as a method for separating the compound (2) from the mixture produced by occurrence of the rearrangement reaction of the double bond in part of the intended diene compound (1).

An example of producing the mixture of the present invention is the reaction product in production of the diene compound (1). If the reaction conditions for producing the diene compound (1) are those enough to induce the rearrangement reaction of the diene compound (1), the compound (2) can exist in the reaction product.

Specific examples of the manner of obtaining the mixture of the present invention, include a reaction product of pyrolysis of the following compound (1B-1), a reaction product of dechlorination reaction of the following compound (1B-2), and so on. In a case where the compound (1B-2) is mixed with the following compound (1B-3) in the dechlorination reaction of the compound (1B-2), the reaction product of the dechlorination reaction can be a mixture of the compound (1) and the compound (2). Here, symbols in the following formulae have the same meanings as those defined above.

$$FCOCR^1R^2CR^3FCFR^4CR^5R^6OCR^7=CR^8R^9 \quad (1B-1),$$

$$CR^1R^2=CR^3CFR^4CR^5R^6OCClR^7—CClR^8R^9 \quad (1B-2) \text{ and}$$

$$CFR^1R^2 CR^3=CR^4CR^5R^6OCClR^7—CClR^8R^9 \quad (1B-3).$$

The compound (1B-3) is a compound that can be readily produced by rearrangement of the double bond in the compound (1B-2).

The mixture of the present invention may include another compound in addition to the diene compound (1) and the compound (2). The other compound is preferably one selected from a compound that can be separated from the diene compound (1) and the rearrangement reaction product of the compound (2), and a compound that does not react with the diene compound (1), the compound (2) and the rearrangement reaction product of the compound (2), and there are no particular restrictions on the other compound.

In the present invention, the Claisen rearrangement reaction is induced with the compound (2) in the mixture to produce the product comprising the Claisen rearrangement reaction product and the diene compound (1). The Claisen rearrangement reaction can be carried out by bringing the mixture to a temperature higher than that at which the Claisen rearrangement reaction can take place, and normally it can be carried out by heating. The temperature in heating is preferably one higher than the boiling points of the diene compound (1) and the compound (2), and normally it is preferably from 150 to 400° C., particularly preferably from 200° C. to 350° C., especially preferably from 270 to 320° C. In a case where the mixture is a product of a low temperature reaction and where the Claisen rearrangement reaction can occur at or below the room temperature, the Claisen rearrangement reaction can proceed only by keeping the reaction product at the room temperature.

The Claisen rearrangement reaction is preferably carried out as a vapor-phase reaction, and it is preferable to carry out the rearrangement reaction by heating the mixture of the present invention in vapor phase. Furthermore, since the reaction rate of the rearrangement reaction of the compound (2) is dependent on temperature, the reaction time can be shortened when it is carried out as a vapor-phase reaction which can set the reaction temperature high. The shorter reaction time has the remarkable advantage that only the intended Claisen rearrangement reaction can proceed while preventing polymerization of the compound (1) and the compound (2) which are polymerizable compounds.

In the vapor-phase reaction, it is preferred to carry out the heating of the mixture by introducing it into a vaporizer heated to a temperature higher than the both boiling points of the diene compound (1) and the compound (2), to vaporize the mixture, and then introducing the vaporized mixture into a reactor heated. There are no particular restrictions on the shape or type of the reactor, and a tubular reactor is normally preferable. Furthermore, it is preferable to continuously introduce the mixture into the reactor and to continuously discharge the product. The residence time of the gaseous mixture in the reactor is preferably approximately from 1 to 30 seconds, particularly preferably from 4 to 20 seconds, especially preferably from 6 to 15 seconds. By setting the residence time in the appropriate range, the intended Claisen rearrangement reaction can proceed without the polymerization.

Furthermore, the diluted vapor of the reaction mixture is preferably diluted by an inert gas, or an inert solvent that turns into a gas at the reaction temperature. The inert gas may be argon gas, nitrogen gas, helium gas or the like. The amount of the inert gas is preferably from 3 to 10 times the volume of the raw mixture gas. The presence of the inert gas can improve the operationality of the reaction. Furthermore, the presence of the inert solvent can prevent polymerization. The inert solvent is selected from those that turn into gas at the temperature when heated and are inert at the temperature when heated, and may be selected, for example, from perfluorocarbons, chlorinated fluorinated hydrocarbons and the like. The amount of the inert solvent is preferably determined so that the total concentration of the diene compound (1) and the compound (2) becomes approximately from 10 to 30% by mol.

On the other hand, where the Claisen rearrangement reaction is carried out as a liquid-phase reaction, it is preferable to carry out the reaction by heating under pressure.

Furthermore, in a case where the diene compound (1), the compound (2) and the rearrangement reaction product are polymerizable compounds, the Claisen rearrangement reaction is preferably carried out in the presence of a polymerization inhibitor, regardless of whether the reaction is done in vapor phase or in liquid phase. The polymerization inhibitor may be selected from α-pinene, diphenylpicrylhydrazyl, tri-p-nitrophenylmethyl, p-benzoquinone, p-tert-butylcatechol, nitrosobenzene, picric acid, dithiobenzoyl disulfide and the like. The amount of the polymerization inhibitor to be used is preferably from 0.01 to 10% by mass, particularly preferably from 0.01 to 5% by mass, especially preferably from 0.2 to less than 1% by mass based on the total amount of the diene compound (1) and the compound (2).

Furthermore, in a case where the Claisen rearrangement reaction is carried out in a liquid-phase reaction, the reaction system is preferably thoroughly deaerated in order to prevent the polymerization. The liquid-phase reaction may be carried out in the presence of a solvent. As the solvent, a polar solvent is preferred. Furthermore, the reaction may be carried out in the presence of a catalyst (an acid or the like), if necessary.

In the present invention, the Claisen rearrangement reaction is induced in the compound (2). Since the compound (2) is a compound that can take a 6-membered ring transition state as shown in the following formula, the Claisen rearrangement proceeds to form the rearrangement reaction product represented by the following formula (3).

$$CR^5CR^6{=}CR^4CR^3(CFR^1R^2)CR^8R^9CR^7{=}O \quad (3)$$

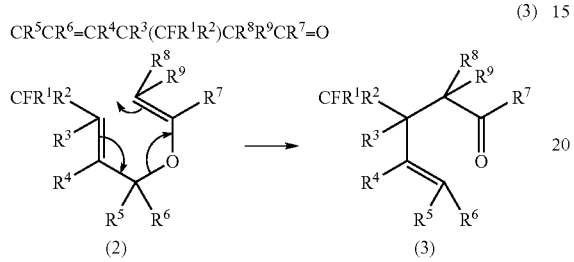

The Claisen rearrangement reaction product is normally the compound (3), but, in the case of the compound (2a) wherein $R^3$ and $R^7$ in the compound (2) independently are a fluorine atom, the following compound (3a) can be produced depending on the reaction conditions. Here, symbols in the following formulae have the same meanings as those defined above.

$$CR^5CR^6{=}CR^4C(CFR^1R^2){=}CR^8R^9 \quad (3a)$$

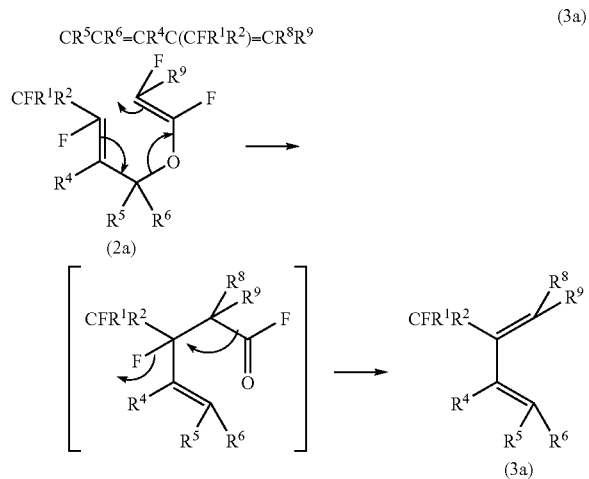

A condition under which the compound (3a) can be produced, is that the Claisen rearrangement reaction is carried out by heating in the presence of soda ash or glass beads.

Specific examples of the compound (3) include the following compounds.

$CF_2{=}CF{-}CF(CF_3){-}CF_2{-}COF$, $CF_2CF{=}CF_2{-}CF(CF_3){-}CF_2{-}COF$, $CF_2{=}C(OCF_3){-}CF(CF_3){-}CF_2{-}COF$, $CF_2{=}CF{-}CF(CH_2F){-}CF_2COF$, $CF_2{=}C(CF_3){-}CH(CHF_2){-}CF_2{-}COF$, $CF_2{=}CF{-}CF(CHF_2){-}CF_2{-}COF$, $CF_2{=}C(CF_3){-}CH(CF_3){-}CF_2{-}COF$, $CH_2{=}CF{-}CF(CF_3){-}CF_2COF$, $CCl_2{=}CF{-}CF(CF_3){-}CF_2{-}COF$ and $CHCl{=}CF{-}CF(CF_3){-}CF_2{-}COF$.

Specific examples of the compound (3a) include the following compounds.

$CF_2{=}CF{-}C(CF_3){=}CF_2$, $CF_2CF{=}CF_2{-}C(CF_3){=}CF_2$, $CF_2{=}C(OCF_3){-}CF(CF_3){=}CF_2$.

$CF_2{=}CF{-}CF(CH_2F){=}CF_2$, $CF_2{=}CF{-}C(CHF_2){=}CF_2$ $CH_2{=}CF{-}C(CF_3){=}CF_2$, $CCl_2{=}CF{-}C(CF_3){=}CF_2$ and $CHCl{=}CF{-}C(CF_3){=}CF_2$.

On the other hand, since the diene compound (1) is a compound that cannot take a 6-membered ring transition state, it can be directly recovered from the reaction product after the Claisen rearrangement reaction.

The present invention involves one of the following steps, (Method 1); the diene compound (1) is separated from the Claisen rearrangement reaction product, or (Method 2); the Claisen rearrangement reaction product is converted into a derivative and then the diene compound (1) is separated from the derivative of the Claisen rearrangement reaction product, thereby obtaining the diene compound (1) in high purity.

In the Method 1, there are no particular restrictions on a method for separating the diene compound (1) and the rearrangement reaction product in the resulting product from each other and applicable methods include distillation, chromatography, washing with water, and so on. For example, if the boiling points of the diene compound (1) and the Claisen rearrangement reaction product are different from each other, they can be easily separated by distillation. Furthermore, in a case where a water-soluble group (e.g., —COF group, —COCl group, etc.) is present at the terminal of the rearrangement reaction product, they can be easily separated from each other by washing with water. In addition, another separating method (e.g., separation by chromatography) may be adopted. In a case where the Claisen rearrangement reaction product is the compound (3), the compound (3) has the same molecular weight as that of the diene compound (1) but a carbonyl group having a different polarity is present in the compound (3); therefore, it can be easily separated from the diene compound (1) by chromatography, distillation, a method of forming a hydrate at the carbonyl group, or the like.

In the Method 2, after the Claisen rearrangement reaction product is converted into a derivative, the diene compound (1) is separated from the derivative of the Claisen rearrangement reaction product. For example, when the rearrangement reaction product is the compound (3), it converts to another derivative by using the reactivity of the carbonyl moiety, and then separate the derivative from the diene compound (1) by a known method. Some of other methods for converting the compound (3) into another derivative are a method of increasing the molecular weight by an addition reaction, a method of reducing the carbonyl group to a hydroxyl group, and so on. Furthermore, the separation method after the derivative forming step can be selected from methods similar to those in the Method 1.

According to the method of the present invention, the compound (1) is separated from the mixture of the compound (1) and the compound (2) by making use of the Claisen rearrangement reaction, thereby obtaining the compound (1) in higher purity. When the compound (1) obtained by the method of the present invention is a polymerizable compound, a fluorocarbon polymer with a high molecular weight can be produced, because the compound (2) which interferes with the polymerization is separated off.

Furthermore, the present invention also provides the production method of the following compound (3) comprising carrying out the Claisen rearrangement reaction in the compound (2). The present invention also provides the production method of the following compound (3a) comprising heating the following compound (2a) in the presence of the glass beads or soda ash. Here, symbols in the formulae have the same meanings as those defined above. These production methods can be carried out in the same manner as the reaction in the Claisen rearrangement reaction in the mixture of the compound (2) and the compound (1).

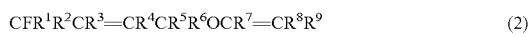

$$CFR^1R^2CR^3=CR^4CR^5R^6OCR^7=CR^8R^9 \quad (2)$$

$$CR^5R^6=CR^4CR^3(CFR^1R^2)CR^8R^9CR^7=O \quad (3)$$

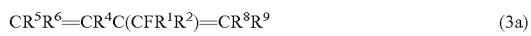

$$CR^5R^6=CR^4C(CFR^1R^2)=CR^8R^9 \quad (3a)$$

EXAMPLES

Now, the present invention will be described below in further detail with examples thereof. It is, however, noted that the present invention is by no means intended to be limited to these examples.

Reference Example 1

An INCONEL 1-inch tubular reactor was filled with glass beads in a filling height of 20 cm and heated to 330° C. A compound represented by the formula $CF_2ClCFClO(CF_2)_4COF$ (300 g, 0.725 mol) was diluted to 10 vol % with nitrogen gas and introduced into the reaction tube. A reaction was carried out while controlling a gas velocity at 2.0 cm/s and maintaining a residence time of the reaction gas at 10 seconds in the glass-bead layer. The outlet gas of the tubular reactor was trapped by a dry ice-ethanol trap. The trapped liquid (250 g) was analyzed by gas chromatography (GC), and it was found that the conversion of the starting material was 99.9%, $CF_2ClCFClOCF_2CF_2CF=CF_2$ was produced in the selectivity of 90.4%, and $CF_2ClCFClOCF_2CF=CFCF_3$ (a mixture of the cis form and trans form) resulting from rearrangement of the double bond was produced in the selectivity of 4.8%. It was attempted to separate $CF_2ClCFClOCF_2CF=CFCF_3$ by distillation purification and by silica gel column chromatography, but failed to separate it.

Reference Example 2

The mixture (0.7 mol) of the products obtained in Reference Example 1 was put in a dropping funnel. On the other hand, dimethylformamide (7.0 mol) and zinc (3.5 mol) were charged in a 1 L flask. A distillation column was attached to the upper part of the 1 L flask, and distillation was conducted while the mixture was continuously dropwise added from the dropping funnel. A dechlorinated product as a distillation product was continuously distilled out. The distilled liquid (156 g) was analyzed by GC, and $CF_2=CFOCF_2CF_2CF=CF_2$ was found to be obtained in the yield of 72%.

The liquid contained $CF_2=CFOCF_2CF=CFCF_3$, which is a dechlorinated product of $CF_2ClCFClOCF_2CF=CFCF_3$, and the amount thereof was 10% (% by peak area in GC) relative to $CF_2=CFOCF_2CF_2CF=CF_2$. It was found that $CF_2=CFOCF_2CF=CFCF_3$ was not successfully separated off by distillation purification and by silica gel column chromatography.

Example 1

The distilled liquid (50 g) containing $CF_2=CFOCF_2CF_2CF=CF_2$ and $CF_2=CFOCF_2CF=CFCF_3$, obtained in Reference Example 2, was introduced into a vaporizer heated at 100° C. to vaporize, and then was diluted to 30 vol % with nitrogen gas. The gas was introduced into a 100 cm, ½-inch reactor of INCONEL heated at 310° C. The gas velocity was controlled at 8.3 cm/s and the residence time of the reaction gas was maintained at 12 seconds. The products in outlet gas was collected by passing through a glass trap cooled at −78° C. by dry ice-ethanol, and 48 g of liquid was recovered. The recovered liquid was analyzed by GC and the analysis confirmed the presence of $CF_2=CFOCF_2CF_2CF=CF_2$ and $CF_2=CFCF(CF_3)CF_2COF$ and the absence of $CF_2=CFOCF_2CF=CFCF_3$. The yield of $CF_2=CFOCF_2CF_2CF=CF_2$ was 92%. The recovered liquid was distilled to obtain $CF_2=CFOCF_2CF_2CF=CF_2$ with the GC purity of at least 99.9%.

Example 2

The distilled liquid (30 g) obtained in Reference Example 2 was mixed with $CF_2ClCF_2CHClF$ (R225cb, 70 g) to obtain a solution. This solution was vaporized in a vaporizer heated at 100° C., and then was diluted to 90 vol % with nitrogen gas. The gas was introduced in a 100 cm, ½-inch tubular reactor of INCONEL heated at 310° C. The gas velocity was controlled at 8.3 cm/s and the residence time of the reaction gas was maintained at 12 seconds. The reaction products of outlet gas was collected by passing through a glass trap cooled at 0° C. by an ice water trap, and recovered (98 g). The recovered liquid was analyzed by GC and the analysis confirmed the presence of $CF_2=CFOCF_2CF_2CF=CF_2$ and $CF_2=CFCF(CF_3)CF_2COF$, and the absence of $CF_2=CFOCF_2CF=CFCF_3$. The yield of $CF_2=CFOCF_2CF_2CF=CF_2$ was 93%. The recovered liquid was distilled to obtain $CF_2=CFOCF_2CF_2CF=CF_2$ in the GC purity of at least 99.9%.

Example 3

The distilled liquid (50 g) obtained in Reference Example 2 was preliminarily vaporized in a vaporizer heated at 100° C., and then was directly introduced to a 100 cm, ½-inch tubular reactor of INCONEL heated at 310° C. The gas velocity was controlled at 8.3 cm/s and the residence time of the reaction gas was maintained at 12 seconds. The reaction products in the outlet gas was collected by passing through the glass trap cooled at 0° C. by an ice water trap, and recovered (48 g). The recovered liquid was analyzed by GC and the analysis confirmed the presence of $CF_2=CFOCF_2CF_2CF=CF_2$ and $CF_2=CFCF(CF_3)CF_2COF$, and the absence of $CF_2=CFOCF_2CF=CFCF_3$.

Polymerization of $CF_2=CFOCF_2CF_2CF=CF_2$ was slightly recognized, and the yield of $CF_2=CFOCF_2CF_2CF=CF_2$ was 79%. The recovered liquid was distilled to obtain $CF_2=CFOCF_2CF_2CF=CF_2$ in the GC purity of at least 99.9%.

Example 4

A polymerization inhibitor (2-pinene, 1 g) was added to the distilled liquid (49 g) obtained in Reference Example 2 to obtain a solution. This solution was vaporized in a vaporizer heated at 100° C., and then was introduced into a 100 cm, ½-inch tubular reactor of INCONEL heated at 310° C. The gas velocity was controlled at 8.3 cm/s and the residence time of the reaction gas was maintained at 12 seconds. The reaction products in outlet gas was collected by passing through a glass trap cooled at 0° C. by an ice water trap, and recovered (48 g). The recovered liquid was analyzed by GC and the analysis confirmed the presence of $CF_2=CFOCF_2CF_2CF=CF_2$ and $CF_2=CFCF(CF_3)CF_2COF$, and the absence of $CF_2=CFOCF_2CF=CFCF_3$. The yield of $CF_2=CFOCF_2CF_2CF=CF_2$ was 92%. The recovered liquid was distilled to obtain $CF_2=CFOCF_2CF_2CF=CF_2$ in the GC purity of at least 99.9%.

Example 5

$CF_2=CFOCF_2CF_2CF=CF_2$ (150 g) not containing $CF_2=CFOCF_2CF=CFCF_3$, obtained in Example 1, methanol (23.7 g), an initiator ($[(CH_3)_2CHOCO]_2$, 3 g), a dispersant (6.7 g, trade name: LEVENOL WZ manufactured by Kao Corporation) and ultrapure water (800 g) were charged in a 1 L separable flask, and stirred for 26 hours in total of 20 hours at 40° C. and 6 hours at 50° C. to effect polymerization. The resultant slurry was made to pass through a 4 μm filtration film, and the filter cake was dried at 100° C. for 20 hours, thereby obtaining a cyclic polymer having a repeating unit represented by the following formula. The yield of the cyclic polymer was 93% and the intrinsic viscosity thereof was 0.35.

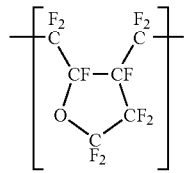

Comparative Example 1

A polymerization reaction was conducted in the same manner as in Example 5, using $CF_2=CFOCF_2CF_2CF=CF_2$ containing 0.08% by mass of $CF_2=CFOCF_2CF=CFCF_3$. The yield of the cyclic polymer was 87% and the intrinsic viscosity was 0.31.

Comparative Example 2

A polymerization reaction was conducted in the same manner as in Example 5, using $CF_2=CFOCF_2CF_2CF=CF_2$ containing 0.15% by mass of $CF_2=CFOCF_2CF=CFCF_3$. The yield of the cyclic polymer was 85% and the intrinsic viscosity was 0.30.

INDUSTRIAL APPLICABILITY

According to the method of the present invention, the compound (2) is separated from the mixture containing the compound (1) and the compound (2) having the same molecular formula and molecular weight as those of the compound (1), without using any special reagent or complicated technique, whereby it is feasible to obtain the compound (1) in high purity. In a case where the compound (1) obtained by the method of the present invention is a polymerizable compound, the method of the present invention also permits the compound (2) to be separated off without substantial polymerization of the compound (1). Furthermore, in the case of the compound (1) being polymerizable, because the compound (2) which interferes with polymerization is separated off, a fluorocarbon polymer having a higher molecular weight can be produced by polymerization of the compound (1).

The entire disclosure of Japanese Patent Application No. 2001-378924 filed on Dec. 12, 2001 including specification, claims and summary is incorporated herein by reference in its entirety.

What is claimed is:

1. A method for producing a diene compound, which comprises:
   inducing a Claisen rearrangement reaction of a compound having formula (2) in a mixture comprising the diene compound represented by formula (1) and the compound having formula (2), thereby producing a Claisen rearrangement reaction product comprised of the diene compound having formula (1), which is the desired rearrangement product, and the compound having formula (2)

$$CR^1R^2=CR^3CFR^4CR^5R^6OCR^7=CR^8R^9 \quad (1)$$

$$CFR^1R^2CR^3=CR^4CR^5R^6OCR^7=CR^8R^9 \quad (2)$$

wherein $R^1$ to $R^9$, which may be the same or different from each other, represent hydrogen, halogen, a monovalent hydrocarbon group, an etheric oxygen atom-containing monovalent hydrocarbon group, a halogenated monovalent hydrocarbon group or a halogenated etheric oxygen atom-containing monovalent hydrocarbon group; and separating the diene compound represented by formula (1) from the Claisen rearrangement reaction product, or
   converting the Claisen rearrangement reaction product into a derivative thereof and then separating the diene compound having formula (1) from the derivative of the Claisen rearrangement reaction:product, thereby producing the compound having formula (1) in high purity.

2. The method according to claim 1, wherein a compound having formula (3) is a product of the Claisen rearrangement reaction:

$$CR^5R^6=CR^4CR^3(CFR^1R^2)CR^8R^9CR^7=O \quad (3)$$

wherein $R^1$ to $R^9$ have the same meanings as defined above.

3. The method according to claim 1, wherein a compound having formula (3a) below is produced by the Claisen rearrangement reaction and the compound having formula (2) is a compound having the scope of formula (2a):

$$CFR^1R^2CF=CR^4CR^5R^6OCF=CR^8R^9 \quad (2a)$$

$$CR^5R^6=CR^4C(CFR^1R^2)=CR^8R^9 \quad (3a)$$

wherein $R^1$ to $R^9$ have the same meanings as defined above.

4. The method according to claim 1, wherein $R^1$ to $R^9$, which may be the same or different from each other, are fluorine, hydrogen, chlorine, trifluoromethyl or trifluoromethoxy.

5. The method according to claim 4, wherein all of $R^1$ to $R^9$ are fluorine.

6. The method according to claim 1, wherein the Claisen rearrangement reaction is induced by heating the mixture in the vapor phase.

7. The method according to claim 6, wherein the Claisen rearrangement reaction is induced in the presence of an inert gas, or an inert solvent which turns into a gas at reaction temperature.

8. The method according to claim 1, wherein the Claisen rearrangement reaction is conducted in the presence of a polymerization inhibitor.

9. The method according to claim 1, wherein the Claisen rearrangement reaction is induced by heating the mixture at a temperature ranging from 150 to 400° C.

10. The method according to claim 1, wherein the compound having formula (2) is a compound produced by a rearrangement reaction of a double bond in the compound represented by the formula (1), or is a compound produced by a dechlorination reaction of a compound having formula (1B-3):

$$CFR^1R^2CR^3=CR^4CR^5R^6OCClR^7-CClR^8R^9 \quad (1B\text{-}3)$$

wherein $R^1$ to $R^9$ have the same meanings as defined above.

11. A method for producing a fluorine-containing polymer, which comprises:
polymerizing the diene compound of formula (1) that is prepared in high purity by the method defined in claim 1.

12. A method for producing a diene compound, which comprises:
heating a compound having formula (2a):

$$CFR^1R^2CF=CR^4CR^5R^6OCF=CR^8R^9 \quad (2a)$$

wherein $R^1$, $R^2$, $R^4$, $R^5$, $R^6$, $R^8$ and $R^9$, which may be the same or different from each are each hydrogen, halogen, a monovalent hydrocarbon group, an etheric oxygen atom-containing monovalent hydrocarbon group, a halogenated monovalent hydrocarbon group or a halogenated etheric oxygen atom-containing monovalent hydrocarbon group, in the presence of soda ash or glass beads, thereby producing a product of formula (3a):

$$CR^5R^6=CR^4C(CFR^1R^2)=CR^8R^9 \quad (3a)$$

wherein $R^1$ to $R^9$ have the same meanings as defined above.

* * * * *